(12) United States Patent
Kashiwagi et al.

(10) Patent No.: US 7,878,710 B2
(45) Date of Patent: Feb. 1, 2011

(54) X-RAY RADIATION IMAGE PHOTOGRAPHING APPARATUS

(75) Inventors: Nobuhiko Kashiwagi, Ashigarakami-gun (JP); Tomonari Sendai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/398,780

(22) Filed: Mar. 5, 2009

(65) Prior Publication Data
US 2009/0225936 A1 Sep. 10, 2009

(30) Foreign Application Priority Data
Mar. 6, 2008 (JP) .............................. 2008-056328

(51) Int. Cl.
*A61B 6/08* (2006.01)
(52) U.S. Cl. ..................................... 378/206
(58) Field of Classification Search .................. 378/37, 378/206
See application file for complete search history.

(56) References Cited
U.S. PATENT DOCUMENTS
6,268,614 B1  7/2001  Imai

2006/0120513 A1 * 6/2006 Buttner et al. .............. 378/206
2008/0200876 A1 * 8/2008 Kukuk et al. ................ 604/116

FOREIGN PATENT DOCUMENTS
WO    2007/023050 A1    3/2007

* cited by examiner

*Primary Examiner*—Chih-Cheng G Kao
(74) *Attorney, Agent, or Firm*—Sughrue Mion, PLLC

(57) ABSTRACT

A radiation image photographing apparatus is formed with a photographing unit that includes a radiation emission means for emitting radiation, a radiation image detection means for recording a radiation image, a region of interest indication means for indicating a mark on a site of a subject corresponding to the region of interest specified in the radiation image, and the like; a computer having an input means, such as a mouse; and a monitor, in which a radiation image obtained by photographing is displayed on the monitor to have the user to specify a region of interest through the input means, and when coordinate information of the region of interest in the image is received from the computer, photographing unit, based on this, controls the region of interest indication means to automatically indicate a mark on a site of the subject corresponding to the region of interest.

6 Claims, 3 Drawing Sheets

X-RAY RADIATION IMAGE PHOTOGRAPHING APPARATUS

BACKGROUND OF THE INVENTION

1. Field of the Invention

The present invention relates to a radiation image photographing apparatus that photographs a radiation image of a subject and is capable of indicating a region of interest on the subject using, for example, laser light or the like.

2. Description of the Related Art

Various types of radiation detectors that record radiation images of subjects by receiving radiation transmitted through the subjects have been proposed and put into practical use in the medical field and the like.

For example, a radiation image detector that uses a semiconductor, such as amorphous selenium or the like, that generates charges by receiving radiation is known as describe, for example, in U.S. Pat. No. 6,268,614, and so-called optical readout type and TFT readout type are proposed as such radiation detectors.

Use of such a radiation detector allows image information to be acquired as digital data, whereby the compatibility of the image information with a diagnosis support system that employs a computer may be increased.

In the mean time, an apparatus that indicates a mark on a region of interest of a subject using a laser marker is proposed as described, for example, in International Patent Publication No. WO/2007/023050. For example, when an abnormal site, such as cancer or the like, is found in a photographed radiation image, a laser marker is emitted on an area of the subject corresponding to the abnormal site to indicate a mark on the area, thereby assisting a doctor or the like in obtaining a biological sample by puncturing into the abnormal region with a needle.

When such a laser marker is used, the position where the mark is indicated by the marker has hitherto been manually controlled by the doctor or radiographer while looking at the photographed radiation image, resulting in inefficiency and relatively low positional accuracy.

The present invention has been developed in view of the circumstances described above, and it is an object of the present invention to provide a radiation image photographing apparatus that photographs a radiation image of a subject and is capable of indicating a mark on a region of interest of the subject using, for example, laser light or the like, which allows automatic positioning control of the mark based on the photographed radiation image.

SUMMARY OF THE INVENTION

A radiation image photographing apparatus of the present invention is an apparatus, including:

a radiation emission means for emitting radiation toward a subject;

a radiation image detection means for recording a radiation image of the subject by receiving radiation transmitted through the subject;

an image display means for displaying the radiation image;

a specification means for specifying a region of interest in the radiation image; and a region of interest indication means for indicating a mark on a site of the subject corresponding to the region of interest in the radiation image specified by the specification means.

Here, as the "radiation image detection means", a solid-state detector capable of providing an image signal representing a radiation image of a subject by converting radiation incident thereon to a charge directly or after converting to light and outputting the charge to the outside may be used.

Various types of solid-state detectors are known. For example, from the aspect of charge generation process in which radiation is converted to charges, an optical conversion type solid-state detector in which signal charges obtained by detecting fluorescence emitted from a phosphor when exposed to radiation are tentatively stored in a charge storage section, and the stored signal charges are converted to image signals (electrical signals) and outputted, a direct conversion type solid-state detector in which signal charges generated in a photoconductive layer when exposed to radiation are collected by charge collecting electrodes and tentatively stored in a charge storage section, and the stored signal charges are converted to electrical signals and outputted, and the like are known. From the aspect of charge readout process in which stored charges are read out to the outside, a TFT (thin film transistor) readout type solid-state detector in which the stored charges are read out by scan driving TFTs connected to the storage section, an optical readout type solid-state detector in which stored charges are read out by emitting reading light (reading electromagnetic wave) on the detector, and the like are known. Further, an improved direct conversion type solid-state detector that combines the direct conversion type and optical readout type is also known as proposed by the inventor of the present invention in U.S. Pat. No. 6,268,614.

In the radiation image photographing apparatus according to the present invention described above, the region of interest indication means may be a means that has a laser light source and indicates the mark on the site corresponding to the region of interest by emitting laser light outputted from the laser light source, and the focal point of the laser light source may be placed at the virtual image position of the focal point of the radiation emission means.

Further, a reference point which is opaque to radiation and detectable by the radiation image detection means may be provided between the radiation emission means and the radiation image detection means.

Still further, the region of interest indication means may be calibrated by specifying the reference point in the radiation image as the region of interest by the specification means and based on the difference between the position of the mark indicated by the region of interest indication means in response to the specification and the actual position of the reference point.

Further, position information of the reference point in the radiation image may be obtained automatically based on shape recognition of the reference point.

Still further, the apparatus may include a light detection means for detecting the position of the mark indicated by the region of interest indication means.

According to the radiation image photographing apparatus of the present invention, the apparatus includes a radiation emission means for emitting radiation toward a subject; a radiation image detection means for recording a radiation image of the subject by receiving radiation transmitted through the subject; an image display means for displaying the radiation image; a specification means for specifying a region of interest in the radiation image; and a region of interest indication means for indicating a mark on a site of the subject corresponding to the region of interest in the radiation image specified by the specification means, thereby allowing user specification of a region of interest in a radiation image obtained by photographing and automatic indication of the mark on a site of a subject corresponding to the region of interest specified by the user, so that the mark may be indicated effectively on the subject.

Further, where the region of interest indication means is a means that has a laser light source and indicates the mark on a site corresponding to the region of interest by emitting laser light outputted from the laser light source, and the focal point of the laser light source is placed at the virtual image position of the focal point of the radiation emission means, the mark may be accurately indicated on the site corresponding to the region of interest regardless of a three-dimensional shape of the subject.

Still further, where a reference point which is opaque to radiation and detectable by the radiation image detection means is provided between the radiation emission means and the radiation image detection means, and the region of interest indication means is calibrated by specifying the reference point in the radiation image as the region of interest by the specification means and based on the difference between the position of the mark indicated by the region of interest indication means in response to the specification and the actual position of the reference point, the positional accuracy of automatic indication of the mark may be improved.

Here, automatic acquisition of position information of the reference point in the radiation image based on shape recognition of the reference point or provision of a light detection means for detecting the position of the mark indicated by the region of interest indication means to automatically detect the position of the mark allows saving of user time and improvement of user-friendliness.

DESCRIPTION OF THE PREFERRED EMBODIMENTS

Figure 1:
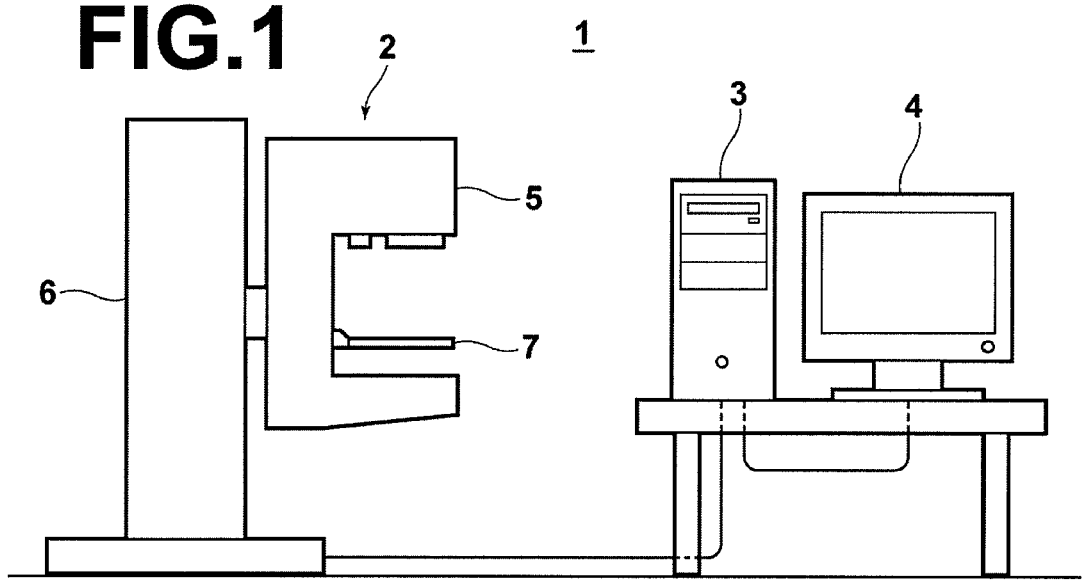
FIG. 1 is a mammography system according to the present invention, illustrating a schematic configuration thereof.
Figure 2:
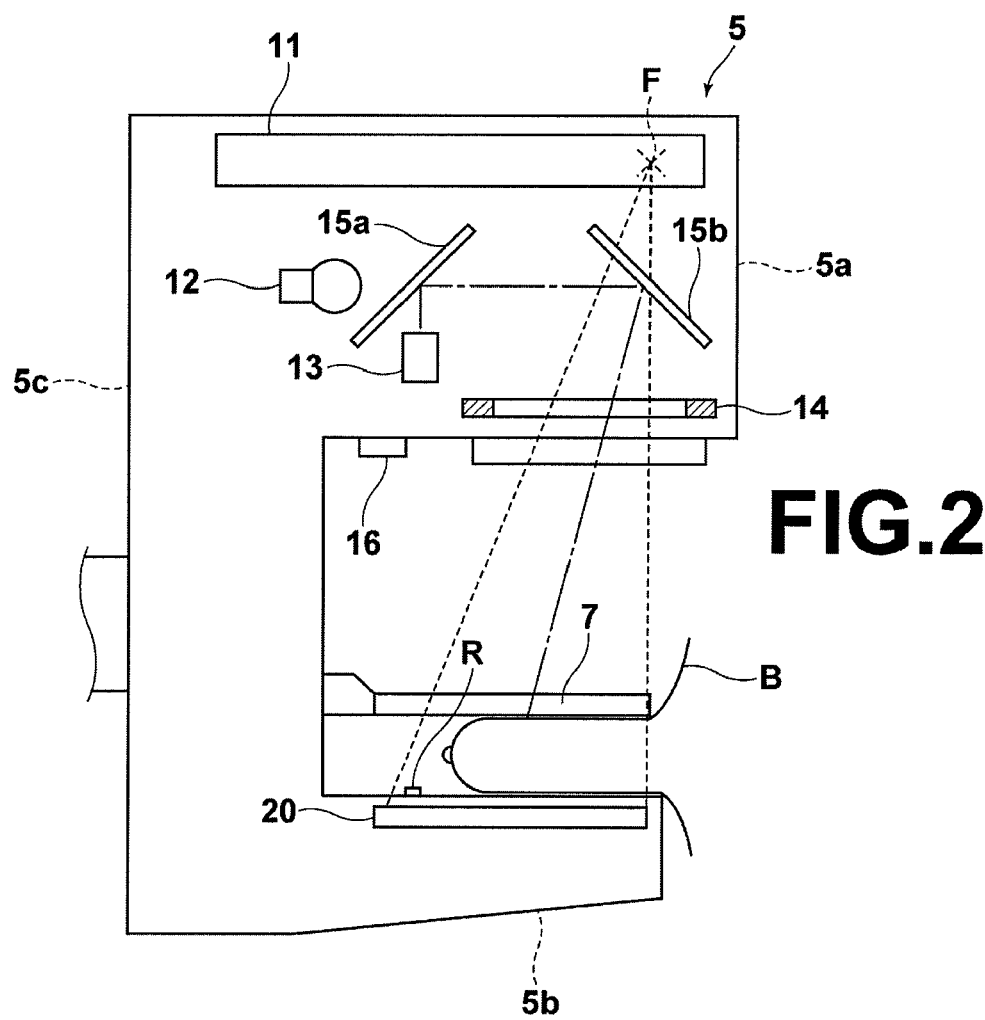
FIG. 2 is a schematic diagram of the mammography machine of the system, illustrating a schematic internal configuration thereof.
Figure 3:
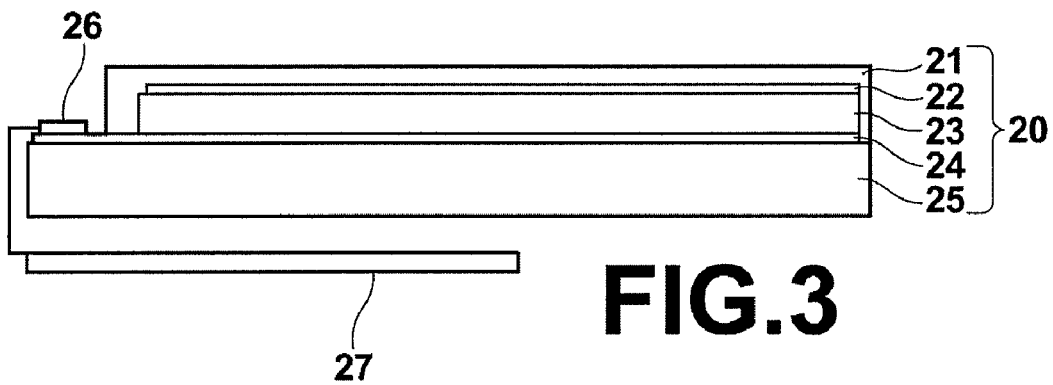
FIG. 3 is a schematic diagram of the solid-state detector used in the mammography machine, illustrating a schematic configuration thereof.
Figure 4:
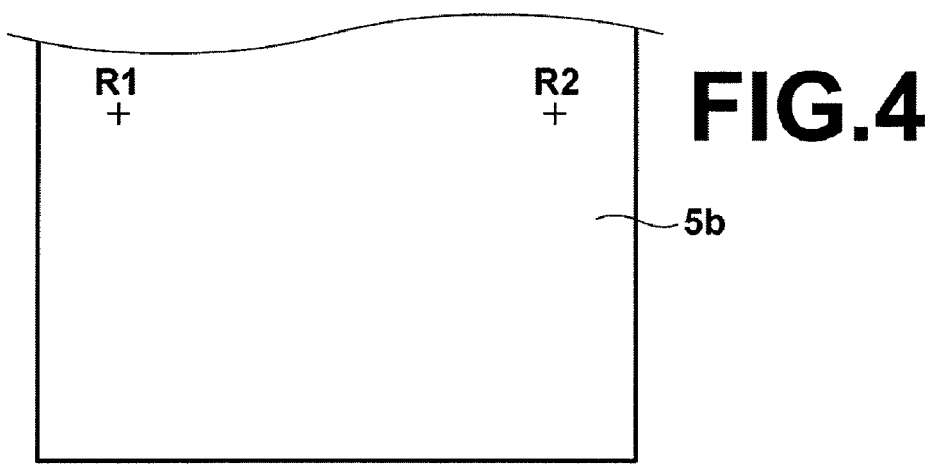
FIG. 4 is a top plan view of the photographing platform section of the mammography machine.

Hereinafter, an exemplary embodiment of the present invention will be described in detail with reference to the accompanying drawings. FIG. 1 is a schematic diagram of the mammography system according to an exemplary embodiment of the present invention. FIG. 2 is a schematic diagram of the mammography machine of the system, illustrating a schematic internal configuration thereof. FIG. 3 is a schematic diagram of the solid-state detector used in the mammography machine, illustrating a schematic configuration thereof FIG. 4 is a top plan view of the photographing platform of the mammography machine.

Mammography system 1 includes mammography machine 2, computer 3 connected to mammography machine 2, and monitor 4 connected to computer 3.

Mammography machine 2 includes body 5 and base 6 that swingably support body 5.

Body 5 is constituted by radiation source housing section 5a that houses inside thereof radiation source 11 and the like, photographing platform section 5b housing therein solid-state detector 20 and the like, and joint section 5c that joins radiation source housing section 5a and photographing platform section 5b, in which joint section 5c is connected to base 6. Further, pressing plate 7 for compressing and holding breast B of a subject from above is attached to joint section 5c.

As shown in FIG. 2, radiation source housing section 5a further includes, other than radiation source 11, illumination light source 12 for illuminating a subject, laser light source 13 for indicating a mark on the subject, mask 14 for limiting the exposure field of radiation, half mirror 15a that transmits light emitted from illumination light source 12 and reflects laser light emitted from laser light source 13, mirror 15b that reflects light emitted from illumination light source 12 and laser light emitted from laser light source 13, and light detection means 16 for detecting the position of laser light emitted on photographing platform section 5b.

Half mirror 15a is adjustable for the angle of the reflection surface, allowing laser light emitted from laser light source 13 to be emitted on any position of photographing platform section 5b. When emitting radiation outputted from radiation source 11, mirror 15b is withdrawable to a position which does not interrupt the emission.

Here, a configuration is adopted such that the focal point of laser light source 13 is placed at the virtual image position of focal point F of radiation source 11. Where the emission position of the laser light is changed by moving half mirror 15a, as in the present embodiment, the focal point of laser light source 13 lies on half mirror 15a, and where it is changed by moving laser light source 13, the focal point lies on the moving axis of the light source.

If the focal point of laser light source 13 is placed at a position other than the virtual image position of focal point F of radiation source 11, the emission position of the laser light is changed due to a three-dimensional shape of the subject, causing difficulties to accurately indicate the mark on the position corresponding to the region of interest in the radiation image. But, as in the present embodiment, the placement of the focal point of laser light source 13 at a position substantially corresponding to the virtual image position of focal point F of radiation source 11 allows accurate indication of the mark on a position of the subject corresponding to the region of interest in the radiation image regardless of the three-dimensional shape of the subject.

In the present embodiment, laser light source 13, half mirror 15a, and mirror 15b constitute a region of interest indication means.

As illustrated in FIG. 3, solid-state detector 20 includes first conductive layer 24 of a-si TFTs, photoconductive layer 23 that generates a charge by receiving radiation and exhibits conductivity, second conductive layer 22, and insulation layer 21 stacked on glass substrate 25 in this order.

First conductive layer 24 includes a TFT for each pixel and the output of each TFT is connected to IC chip 26, which, in turn, is connected to a not shown image signal processing section on printed circuit board 27.

In solid-state detector 20, when radiation is emitted on photoconductive layer 23 while an electric field is formed between first conductive layer 24 and second conductive layer 22, charge pairs are generated in photoconductive layer 23 and latent image charges according to the amount of charge pairs are stored in first conductive layer 24. When reading out the stored latent image charges, the TFTs on first conductive layer 24 are sequentially driven to output an analog signal corresponding to a latent image charge with respect to each pixel, which is detected and combined in the arrangement order of pixels in the image signal processing section. Then, the combined analog signal is A/D converted in a not shown A/D conversion section to generate a digital image signal. The generated digital image signal is transferred from the image processing section to computer 3 via a memory.

As shown in FIG. 4, photographing platform section 5b has thereon two reference points R1, R2 which are opaque to radiation and detectable by solid-state detector 20.

It is note that radiation source 11, illumination light source 12, laser light source 13, mask 14, half mirror 15a, mirror 15b, light detection means 16, solid-state detector 20, and the like are integrally controlled by a not shown control means.

Figure 5:
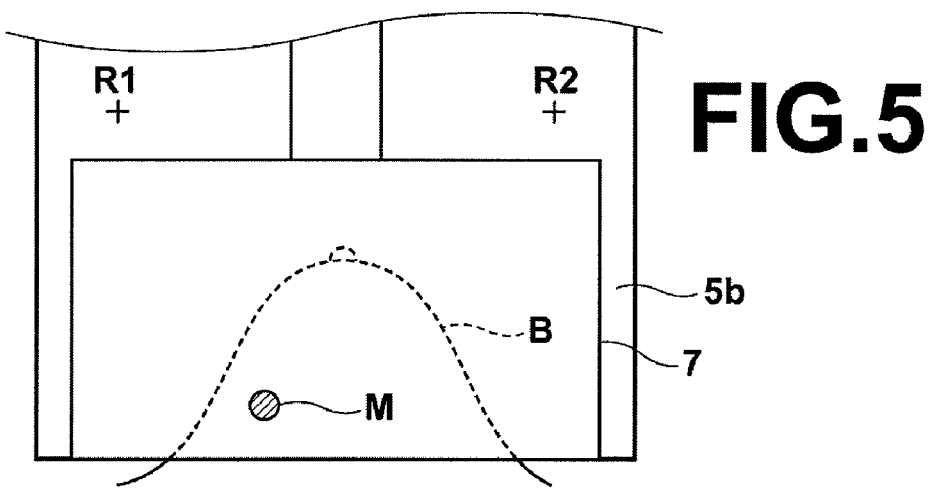
FIG. 5 is a top plan view of the photographing platform section of the mammography machine, illustrating the state in which a breast is compressed thereon by a pressing plate.
Figure 6:
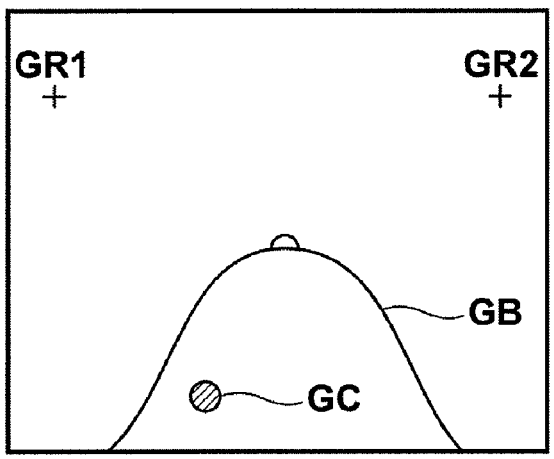
FIG. 6 shows an image photographed under the state shown in FIG. 5.

An operation of mammography system 1 configured in the aforementioned manner will now be described. FIG. 5 is a top plan view of the photographing platform illustrating the state in which a breast is compressed thereon by a pressing plate. FIG. 6 shows an image photographed under the state shown in FIG. 5.

After moving pressing plate 7 to a position to compress and fix breast B on photographing platform section 5b, when a not shown radiation emission switch is depressed by the user, radiation is emitted from radiation source 11 toward solid-state detector 20.

When the radiation is received by solid-state detector 20, latent image charges representing radiation image information are stored therein. The amount of stored latent image charges is substantially proportional to the amount of radiation transmitted through the subject (breast B), thus the latent image charges represent an electrostatic latent image.

After a predetermined time and the photographing is completed by terminating the recording in solid-state detector 20, an analog signal corresponding to the latent image charges is outputted from solid-state detector 20, which is A/D converted in the image signal processing section to generate a digital image signal. The generated digital image signal is transferred from the image signal processing section to computer 3 via a memory.

On receipt of the digital image signal from mammography machine 2, computer 3 causes monitor 4 to display an image like that shown in FIG. 6.

When an abnormal site (GC in FIG. 6), such as cancer or the like, is found in the image displayed on monitor 4, the user specifies the site using an input device, such as a mouse or the like.

On receipt of the region of interest specified by the user, computer 3 sends coordinate information of the specified position in the image to mammography machine 2.

When the region of interest coordinate information is received by mammography machine 2, laser light is emitted from laser light source 13 and the angle of the reflection surface of half mirror 15a is controlled such that the laser light is emitted on a position of the subject corresponding to the region of interest specified in the image. This causes mark M to be indicated on the subject as shown in FIG. 5.

Where indicating mark M on the subject is known in advance, it is desirable that pressing plate 7 be transparent or otherwise pierceable to allow direct writing of a mark on breast B with a marker or to directly obtain a biological sample by puncturing into the abnormal site with a needle.

Figure 7:
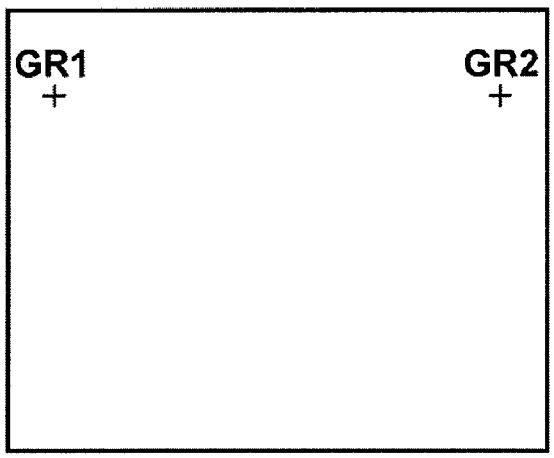
FIG. 7 illustrates an image photographed without placing any subject on the photographing platform section of the mammography machine.
Figure 8:
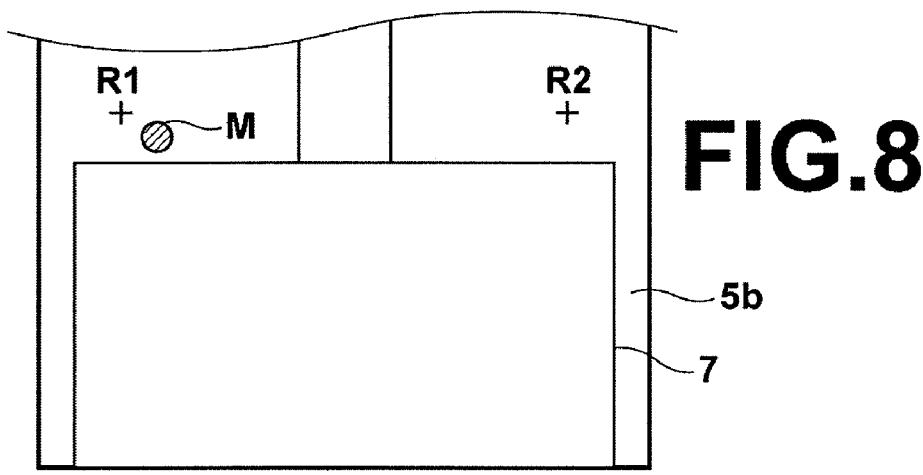
FIG. 8 illustrates the photographing platform section, illustrating the state in which a mark is indicated on the platform according to the reference points in the image shown in FIG. 7.

Next, a calibration process for region of interest indication means of mammography system 1 will be described. FIG. 7 shows an image photographed without placing any subject on the photographing platform section. FIG. 8 shows the photographing platform section, illustrating the state in which a mark is indicated on the platform according to the reference points in the image shown in FIG. 7.

First, photographing is performed without placing any subject on the photographing platform section. Photographing platform section 5b has thereon two reference points R1, R2 which do not transmit radiation and are detectable by solid-state detector 20, so that images GR1, GR2 of two reference points R1, R2 appear in the image, as shown in FIG. 7.

Reference point R can be formed in a shape, for example, + mark, which is easily recognizable in the image, and this allows computer 3 to automatically obtain coordinate information of image GR of reference point R without requiring the user to manually select the image GR of reference point R.

When performing calibration of the region of interest indication means, two reference points R1, R2 or only either one of them may be used. Here, description will be made of a case in which calibration is performed using reference point R1.

Computer 3 sends coordinate information of obtained image GR1 of reference point R1 to mammography machine 2.

When the coordinate information of reference point R1 is received by mammography machine 2, laser light is emitted from laser light source 13 and the angle of the reflection surface of half mirror 15a is controlled such that the laser light is emitted on a position of the subject corresponding to reference point R1 specified in the image. This causes mark M to be indicated on imaging platform 5b as shown in FIG. 8.

Here, mark M should be indicated at the position of reference point R1 when the region of interest indication means has high accuracy. But, as shown in FIG. 8, mark M is indicated at a position different from reference point R1 on photographing platform 5b when the accuracy of the region of interest indication means is degraded due to mechanical error and the like.

Mark M is a bright spot of the laser light, so that it is automatically detectable by light detection means 16 constituted by CCDs and the like. Therefore, the region of interest indication means may be calibrated by adjusting the angle of half mirror 15a based on the difference between the position of the detected mark M and the position of reference point R1.

So far, the exemplary embodiment of the present invention has been described. It will be appreciated that the present invention is not limited to the mammography image photographing system described above, and is applicable to any photographing system.

Further, a TFT readout type has been described as the solid-state detector, but it will be appreciated that the present invention is not limited to this, and the invention may provide identical advantageous effects for other solid-state detectors, such as optical readout type and the like.

What is claimed is:

1. An x-ray radiation image photographing apparatus, comprising:
   an x-ray radiation emission means for emitting x-ray radiation toward a subject;
   an x-ray radiation image detection means for recording an x-ray radiation image of the subject by receiving x-ray radiation transmitted through the subject;
   an image display means for displaying the x-ray radiation image;
   a specification means for specifying a region of interest in the x-ray radiation image;
   a region of interest indication means for indicating a mark on a site of the subject corresponding to the region of interest in the x-ray radiation image specified by the specification means; and wherein:

the region of interest indication means is a means that has a laser light source and indicates the mark on the site corresponding to the region of interest by emitting laser light outputted from the laser light source; and the focal point of the laser light source is placed at the virtual image position of the focal point of the x-ray radiation emission means.

2. The x-ray radiation image photographing apparatus as claimed in claim 1, wherein a reference point which is opaque to x-ray radiation and detectable by the x-ray radiation image detection means is provided between the x-ray radiation emission means and the x-ray radiation image detection means.

3. The x-ray radiation image photographing apparatus as claimed in claim 2, wherein the region of interest indication means is calibrated by specifying the reference point in the x-ray radiation image as the region of interest by the specification means and based on the difference between the position of the mark indicated by the region of interest indication means in response to the specification and the actual position of the reference point.

4. The x-ray radiation image photographing apparatus as claimed in claim 3, wherein position information of the reference point in the x-ray radiation image is obtained automatically based on shape recognition of the reference point.

5. The x-ray radiation image photographing apparatus as claimed in claim 4, wherein the apparatus comprises a light detection means for detecting the position of the mark indicated by the region of interest indication means.

6. The x-ray radiation image photographing apparatus as claimed in claim 3, wherein the apparatus comprises a light detection means for detecting the position of the mark indicated by the region of interest indication means.

* * * * *